United States Patent [19]
Moshfeghi et al.

[11] Patent Number: 6,076,166
[45] Date of Patent: Jun. 13, 2000

[54] PERSONALIZING HOSPITAL INTRANET WEB SITES

[75] Inventors: Mehran Moshfeghi, Sunnyvale; Jun Wang, Copertino; Stephen L. Wong, San Francisco; Yuan-Pin Yu, Sunnyvale; Robert A. Glicksman, San Jose, all of Calif.

[73] Assignee: Philips Electronics North America Corporation, New York, N.Y.

[21] Appl. No.: 08/785,459

[22] Filed: Jan. 17, 1997

[51] Int. Cl.[7] ................................................. G06F 13/00
[52] U.S. Cl. ................................. 713/201; 705/3; 707/9
[58] Field of Search ........................... 395/186, 188.01, 395/187.01, 200.58, 200.57, 200.62, 200.6, 200.63, 200.67; 707/2, 3, 6, 9; 705/2, 3

[56] References Cited

U.S. PATENT DOCUMENTS

| | | | |
|---|---|---|---|
| 5,263,165 | 11/1993 | Janis | 395/725 |
| 5,603,054 | 2/1997 | Theimer et al. | 395/826 |
| 5,689,708 | 11/1997 | Regnier et al. | 395/682 |
| 5,724,567 | 3/1998 | Rose et al. | 395/602 |
| 5,737,539 | 4/1998 | Edelson et al. | 395/203 |
| 5,748,890 | 5/1998 | Goldberg et al. | 395/188.01 |
| 5,754,939 | 5/1998 | Herz et al. | 455/4.2 |
| 5,796,952 | 8/1998 | Davis et al. | 395/200.54 |
| 5,823,879 | 10/1998 | Goldberg et al. | 463/42 |
| 5,826,031 | 10/1998 | Nielsen | 395/200.63 |

OTHER PUBLICATIONS

"Design of an Object–Oriented Multimedia Database for Personalized Multimedia News" by Yuri Quintana, Canadian conference on electrical and computer engineering, vol. 1, May 1996, (New York), pp. 282–285.

"An interactive, personalized, newspaper on the WWW" by Tomonari Kamba and Krishna Bharat, Multimedia computing and networking, vol. 2667, 1996, pp. 290–301.

*Primary Examiner*—Robert W. Beausoliel, Jr.
*Assistant Examiner*—Scott T. Baderman
*Attorney, Agent, or Firm*—Dwight H. Renfrew, Jr.

[57] ABSTRACT

The server includes a layer for dynamically generating web pages and other data objects using scripts, such as graphic, audio and video files, in dependence on stored information indicating the user's needs and preferences, including those presumed from stored information as to the user's function, job, or purpose for being at the hospital, and logged usage profiles, the level of the user's access privileges to confidential patient information, and the computer and physical environments of the user. Notably, the content is generated in dependence on the display resolution and lowest bandwidth link between the server and browser to limit the waiting time for downloads as well as the server load.

23 Claims, 2 Drawing Sheets

PERSONALIZING HOSPITAL INTRANET WEB SITES

BACKGROUND OF THE INVENTION

The present invention relates to information systems including at least one web server which is accessible via a network by user or client equipment operating web browser software. In its particular aspects, the present invention relates to a web system or site which provides web or hypertext pages and/or other data objects that are personalized to the user. While, the present invention addresses personalization in an internal network, known as an intranet, maintained by a hospital or similar institution, many of its principles are also applicable to intranets in other settings, to internets, and to the World Wide Web accessible via the essentially global network known as the Internet.

Intranets are internal information networks which are based on internet standards and protocols. World Wide Web tools are an ideal integration solution for providing health care workers almost immediate access to data from multiple sources in a hospital or other patient care giving setting. Easy and uniform access to medical records, laboratory results, images, notes, transcribed reports, and practice guidelines, can be obtained via the intranet from a web server by user's computer or other web browser capable equipment. However, the presumed needs, declared interests, appropriate levels of access to computer based patient records (CPR), and physical and equipment environments of users differ widely in such a setting.

Conventional personalization systems match users to their declared and/or logged topics of interest but do not take into account their needs presumed from their professional attributes and assigned work, their access levels to CPR or their physical and equipment environments.

SUMMARY OF THE INVENTION

It is an object of the present invention to provide a system wherein a web server is accessible by a web browser via a network, wherein the presumed needs, declared and/or logged topics of interests, access rights to information and environments of users are taken into account in presenting web pages to a user's web browser.

These and other objects are satisfied by a system and method in which web pages are created dynamically based on the user's relationship to the institution or the patient, and the users' function or job, and information access privileges. Furthermore the web pages are created dynamically based on the capabilities of the users' computers, computer bandwidth connection, display characteristics, browser capabilities, and physical room characteristics. In order to achieve this the web server has to be supplied with information about the user and the user's environment. This information can be obtained with the use of web forms, automatic detection of the IP address of the requesting client, server-browser communication, smart cards and/or active badges. Information about user preferences, user's physical and computer environment, and usage profile can be stored at the server. The server can then use all this information to generate personalized content.

Other objects, features and advantages of the present invention will become apparent upon perusal of the following detailed description when taken in conjunction with the appended drawing, wherein:

DETAILED DESCRIPTION OF THE PREFERRED EMBODIMENTS

Figure 1:
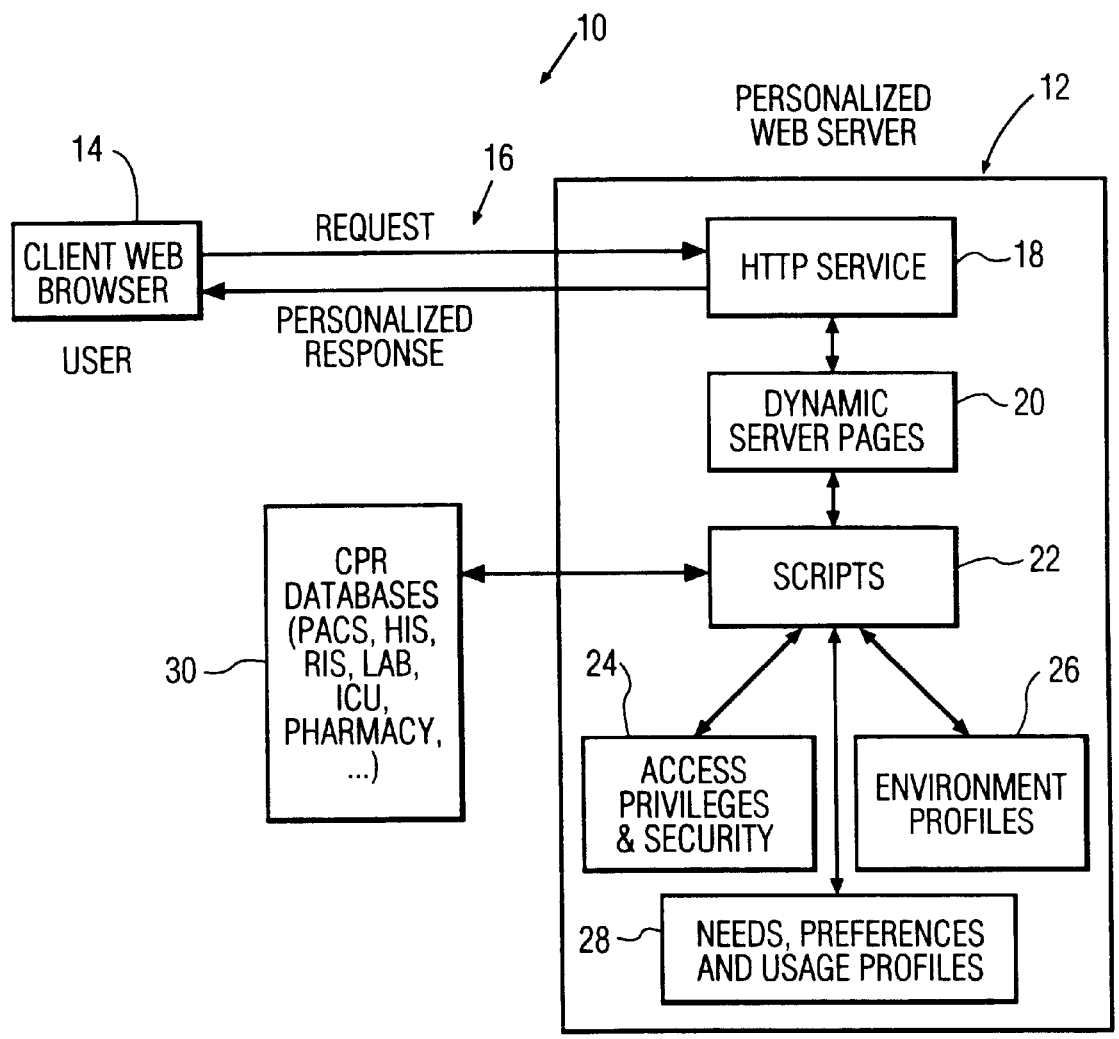
FIG. 1 is a block diagram indicating a web system according to the present invention, including a personalized web server.

Referring to FIG. 1 of the drawing, there is shown a web system 10 for an intranet of a hospital or other care giving institution including a personalized web server 12 which in accordance with the invention includes personalization means 20–28 which will be described hereinafter, and a plurality of user or client computer or other devices capable of operating a web browser, one of which is generally indicated at 14. The user web browser operating equipment 14 and the web server 12 are coupled for bidirectional communication via a network path, generally indicated by 16, which in practice is implemented by one or more wireless or wired network links having associated bandwidths or data rates. The user's equipment may be of a type which varies over the gamut of web browser capable devices including high and low end computer workstations, computer laptops or notebooks, palmtops, personal digital assistants (PDAs) and even televisions, which may be equipped with separate boxes for that purpose. The user may be a physician or employee of the hospital, a patient, or a visitor.

The communication over path 16 includes requests from user equipment 14 and responses from server 12 using the hypertext transport protocol (HTTP) which invoke an operating layer or module 18 of server 14 providing HTTP service. Specifically, user equipment 14 in a known manner requests downloads of particular web pages written in hypertext markup language (HTML) and other data objects (such as images and documents in the form of graphics, audio clips, video clips or cines, and other files). The responses from the web server, in particular the personalized web pages and/or data objects provided, are dynamically generated in layer or module 20 using server scripts 22, that utilize personalizing information maintained in the server's file systems or databases 24 (pertaining to access privileges and security), 26 (pertaining to environment profiles), and 28 (pertaining to user needs, preferences, and usage profiles).

Specifically, server scripts 22 check user access privileges, user preferences, usage log, and environment profile. In the case that the request is for a particular patient, access control for that particular patient is also checked. The outcome is rules for retrieving computer based patient records (CPR) information and rules for generation of web pages. The scripts filter, retrieve, and process the CPR information. The CPR information is distributed in the CPR databases 30 of the Picture Archiving and Communication System (PACS), Hospital Information System (HIS), Radiology Information System (RIS), laboratory system, Intensive Care Unit (ICU) system, Pharmacy system, etc. The scripts then generate dynamic server web pages. The web server sends back the dynamic web pages to the client web browser.

The information necessary or useful to personalize the server's responses include user attributes, user privileges, computer characteristics and network connection, display characteristics, browser capabilities and room characteristics. They are discussed individually as follows:

User Attributes:

User attributes indicate the relationship of the user to the institution or a particular patent, as well as some interests and preferences. They are divided into the categories of staff, patient and visitor, with subcategories as follows:

Staff (physician (dept., function, specialty, interest, education, level of security, favorite browser, etc.), nurse (dept., function specialty, interest, education, authority for information access, favorite browser, etc.), administration (dept., function, interest, etc.)).

Patient (inpatient, outpatient, dept./section (internal medicine, ER, cardiology, etc.), favorite browser).

Visitor (for which patient, first time, regular, etc.).

User Privileges:

User privileges are organized into the following categories:

Write access

Read access

Full view to CPRs of all patients

Full view to CPRs of some patients

Minimal view to CPRs

No view to patient CPRs

Computer characteristics and network connection:

The computer characteristics and network environment aspects of the computer environment are organized into the following categories, and subcategories:

Type (SUN (Ultra 1, Sparc 20, etc.), PC (Pentium, 486, etc.), Mac, etc.)

Operating system (Unix (flavor of Unix), Windows (95, NT, 3.1), MacOS)

Support for audio and video, if any

Lowest Bandwidth Link to Server (bottleneck link): ATM, fast Ethernet, Tl, Ethernet, ISDN, phone line, wireless Display Characteristics:

The display characteristics aspect of the computer environment are organized into the following categories and subcategories:

Spatial resolution (2K×2K, 1K×1K), XGA, SVGA, VGA, etc.

Monochrome or Color

Modulation Transfer Function

Amplitude resolution (number of levels of gray scale and/or of color)

Browser capabilities:

The browser capabilities aspect of the computer environment include the following categories:

Whether or not Java is enabled

Whether or not ActiveX is supported

Which versions of HTML and HTTP are supported

Which plug-ins are supported

Room Characteristics:

The room characteristics indicating the physical environment of the user are organized into the following categories and subcategories:

Function of room (laboratory, film reading, library, public room, private office, home, etc.)

Lighting conditions (dark room, bright room, etc.)

Audio characteristics (loud room, quiet room, etc.)

The foregoing has described under four categories: (A) Access privileges, (B) User preferences, (C) Usage log, and (D) Environment profile. Access privileges depend on federal and state regarding patient confidentiality law. Each hospital may also have their own protocols for ensuring patient confidentiality, data integrity, and security (digital signatures, authentication, and document alteration prevention techniques). The system administrator of the hospital is responsible for maintaining the policies and rules for access to information. Therefore, each user will have a profile which will state what information for each patient they can access. User preferences are entered by the user. The user can enter preferences with the use of a hypertext markup language (HTML) form or Java applets. The usage log for each user is automatically tracked by the server. Environment profile information is obtained from the IP address of the client, client-server browser communication, smart cards, and active badges. These methods of obtaining personalization information will now be explained in more detail.

With respect to the use of forms, the first time that a user accesses the web server he/she will be asked to enter information about himself/herself. This will only have to be done once, unless the user needs to update this information. The form can typically ask for information about the user's department/section, function, specialty, interest, and education level. Since the client can have more than one web browser, users will also have to choose their default browser. The default browser is then started up automatically the next time they log in.

IP addresses of clients requesting information from the server, where they are statically rather than dynamically assigned in the intranet, uniquely identify the client. In such situations, the IP address of the client is automatically detected by the web server when a request comes in. The user environment information which is stored in database or file system 26 at the server includes computer and room information. Therefore the IP address can be used to identify the computer type (e.g. SUN, PC, MAC, etc.), its add-on capabilities (e.g. sound card, video decoding hardware, etc.), its lowest bandwidth connection link to the web server (e.g. ATM, Ethernet, ISDN, wireless, etc.), the resolution of the display to which it is attached (e.g. 2K×2K, 1K×1K, XGA, SVGA, VGA, etc.), the location of the computer (provided it is not mobile), and constraints imposed by the location. System administrators of the hospital's computing facilities would update such system resource information as necessary.

The web server can communicate with the client web browser and detect the browser capabilities (support for Java, ActiveX, versions of HTML and HTTP, plug-ins, etc.). The web server can then serve the appropriate content.

A smart card carried by a person (a credit card sized plastic card that is embedded with a computer chip that can contain personal information) can be read by a computer-based reader at client equipment 14, when a person accesses the intranet. The information read from the smart card may be used not only to prove identity, but also to provide the other user attributes necessary to personalize web content.

Active badges (an Olivetti product) can be used to locate badge holders in a hospital. An active badge emits its identification code at regular intervals via an infrared source. This code can be detected and stored by sensors that are distributed throughout the hospital locations where web browsing can take place. Once the physical location of the web client is determined appropriate content can be presented to them. This is particularly useful for mobile client equipment, such as laptops connected via a telephone or wireless connection. Most computers, however do not get moved and their IP addresses can be used to locate them.

However the personalizing information is collected, as previously noted, it is stored in the database or a file systems 24, 26, and 28 maintained by the server 12. Since the client browser 14 can transmit its capabilities to the web server, so there is no need to store this information.

Once information about the user and his/her environment is known, server scripts 22 can be used to dynamically generate in module 20 the appropriate content for the client. Server scripts can be written in VBScript, JScripts, Java Script, Java, etc.

The following are examples of constraints imposed in personalizing the content:

- The specialty, such as cardiology, of a physician user should be taken into account so that the physician receives only the news and information which is presumed to be of interest.
- A user should only see the information that he/she is privileged to access.
- Rooms that are meant to be quiet rooms such as reporting rooms or library locations should not be exposed to audio files.
- A computer that does not have a sound card should not receive sound files.
- A laptop with a low-speed modem and a small screen should not be exposed to large movie files or large images.
- A browser that does not support ActiveX should not be exposed to ActiveX components.

Personalized content is not only more interesting and relevant to the user. It also makes more efficient usage of network bandwidth and system resources, and reduces server load. It can also reduce document retrieval latency.

With respect to access privileges, it is clear that in a hospital environment different users will have different privileges for access to information based upon their specialty and their relationship to the patient (i.e. patient's attending physician, consulting physician, attending nurse, etc.). For example, not only do different occupations/specialties need different "views" of the CPR which are tailored to their needs but different patient relationships may influence the level of detail presented in sensitive areas. For example, all physicians who treat a patient may see that the patient is undergoing psychiatric treatment, but the details of this sensitive area may be privileged only to the attending psychiatrist and the patient. Also, access to records for certain "VIP" patients (politicians, actors, etc.) may be further restricted than for normal patients, due to the increased potential for adverse publicity and blackmail. Patients should be able to see their own CPRs, in full detail. The same is also true for legal guardians of underage or legally incapable patients.

All users should have a default log-in which has minimal privileges, but is based on location. Therefore, any health care provider inside a hospital may be able to see a summary CPR for any in-patient without a special log-in (other than identifying themselves as health care providers, for example via smart card ID). However, this capability would not be available from outside the firewall guarding the integrity of the intranet.

Security within the intranet system is provided by well known protocols which use digital signatures, authentication, and document alteration prevention techniques.

In addition to user privileges and interests, the CPR may be tailored to the user's equipment and link bandwidth. Many users (physicians, in particular) may have several types of equipment/links e.g. at the office, the hospital, and at home. Further, terminals which are not assigned to particular individuals may be provided at the hospital for referring physicians visiting their in-patients. Each user might, therefore have several profiles. The profile placed into use at any given time could be determined by the client location (IP address) and capabilities (some of which come as CGI environment variables at log-in). Preferably, server 12 personalizes image size (full resolution or minified) and transmission compression (none, lossless, lossy/quality) to the link bandwidth and the capabilities of client equipment 14, so that the user need not wait for large transfers at locations with low speed connections. This applies to video and sound files.

Computers with low-bandwidth connections and/or low-resolution displays need low-resolution images and lower frame-rate video. When considering heterogeneous networks the lowest network bandwidth link between the server and the clients is the limiting factor. Scaling and layered video coding schemes are one method which can be used to multicast one single compressed video stream across heterogeneous networks, computers, and displays. The routers can then send the appropriate number of compressed video layers to the appropriate machines for software or hardware decoding. For example, a high-end workstation with a high resolution display and high bandwidth connection to the server will receive the base layer plus all the enhancement layers. An intermediate computer with a moderate resolution display and a moderate bandwidth connection to the server can receive the base layer plus some of the enhancement layers. A low-end workstation with a low resolution display and a wireless connection, however, will receive only the base layer.

The dynamically generated server pages can be partitioned to accommodate different information categories. A large part of the page will be reserved for personalized information. The personalized information is generated using the user supplied preferences as well as by tracking the user. For example, the web sites and content which the user visits most frequently at specified times and dates can be presented to him/her at similar times and dates. A section of the page can also be reserved for general information which should be seen by everyone. Another part of the page may be reserved just for advertising.

Hospital administrators can decide if they would like to generate extra revenues through advertising. For example, hospitals may choose to charge commercial companies who advertise on the hospital intranet. With a personalized web site the advertising, can be targeted to the appropriate audience. For example, drug companies can target the right specialists for their products. Patients can be exposed to over-the-counter drug advertisements and general diet and health related advertisement. Visitors can be exposed to similar patient-oriented advertisements as well as more general consumer-oriented advertisements.

Figure 2:
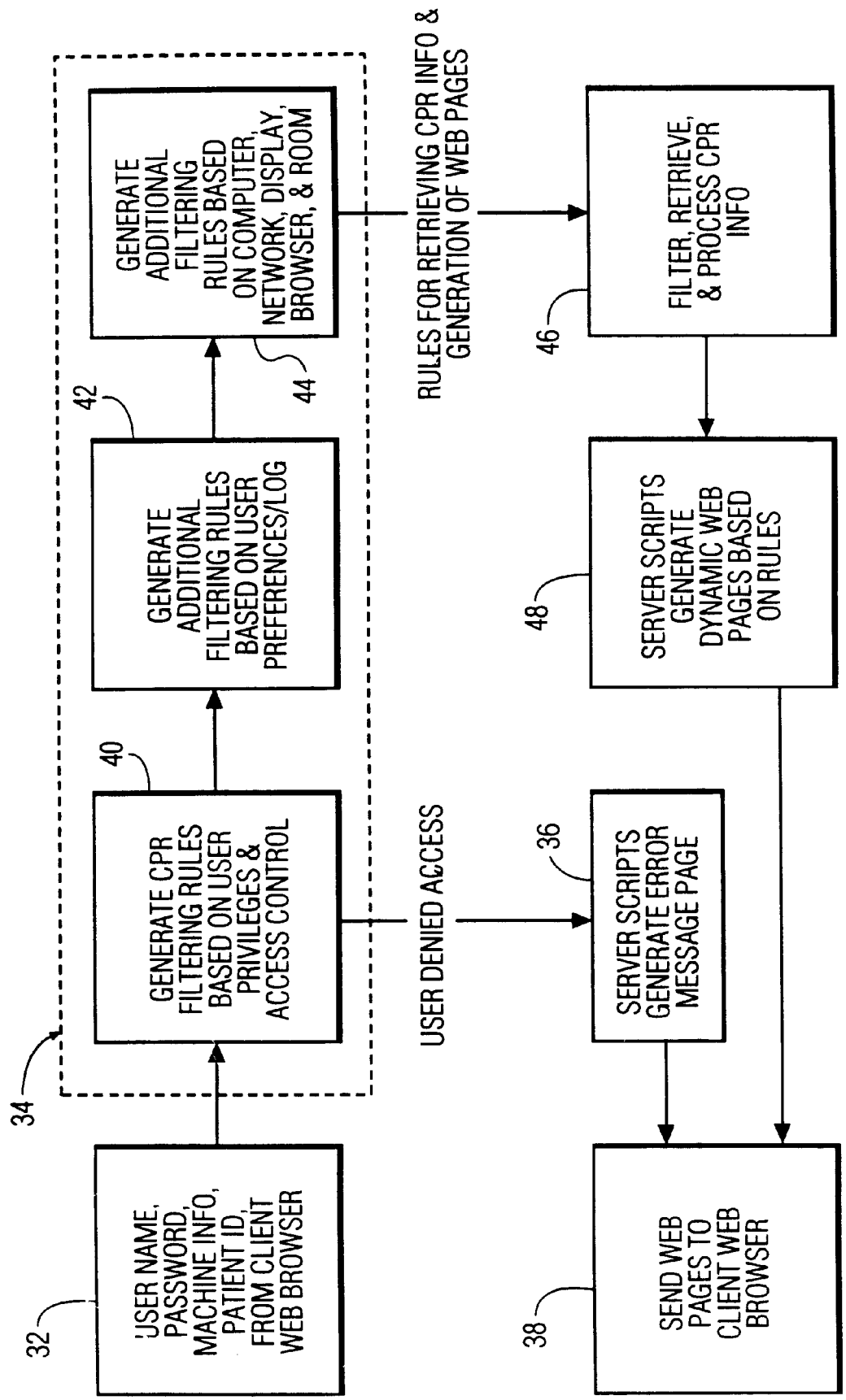
FIG. 2 is a flow chart illustrating how the personalized web server of FIG. 1 uses personalization information to personalize the web pages it generates.

FIG. 2 illustrates how personalization information is used to generate custom web pages. The first step for the user is to enter his/her name and password with a web browser at block 32 which is applied to the rule generation block 34. The latter generates rules for retrieving the appropriate information from the CPR and processing it for a personalized presentation. However, if it is determined in block 34 that the user is unauthorized, then in block 36 server scripts generate an error message web page which is sent to the client at block 38. Information about the computer is automatically obtained at block 34 from the IP address. The user also has to provide at block 32 the ID of the patient which he/she is interested in. This is because user privileges and access control rules are patient dependent.

In rule generation block 34, the highest priority of rules are user privileges and access control rules which are generated in a first stage 40. Thus, if a user is not authorized to view certain information categories for a particular patient then such information is not accessible even if the user indicates otherwise in his/her preferences. User privileges and access control rules state which information the user is allowed to access. User interest rules are then added in second stage 42 so that if the user is authorized to view certain information but is not interested in doing so then he/she is not exposed to uninteresting information. The usage log is also used here to make sure that frequently visited sites and information are not filtered out.

The last set of rules, which are generated in third stage 44, take into account the user's environment such as capabilities of the computer, network connection, display, browser, and room characteristics. Thus, if the display of the user can not handle high-resolution images low resolution images should be presented to the user, even if he/she has requested otherwise. There can be trade-offs for certain situations. For example, if the network connection of the user is slow but the display resolution is high the user can view high-resolution images and video data, provided he/she is willing to wait a long time. The user should be given the choice to make that decision if it does not affect anyone else.

The outcome of the three stages 40, 42, 44 of rule generation are rules for retrieving CPR information and rules for generation of web pages. At block 46, using these rules, server scripts retrieve the appropriate CPR information. The scripts also process the information at this point so that it is personalized for the user. For example, high-resolution images/video may be sampled at lower resolution, or numerical information may be presented graphically. At block 48, server scripts dynamically generate web pages for the client. The generated web pages are then sent, at block 38, to the browser of the client.

It should now be apparent that the objects of the present invention have been fulfilled. While the present invention has been described in particular detail, it should also be appreciated that numerous modifications are possible within the intended spirit and scope of the invention.

What is claimed is:

1. An information system comprising
   a network and
   at least one web server which is accessible via the network by user equipment operating a web browser, which server comprises
   means for dynamically generating content that is personalized to the user taking into account user equipment environment information provided or stored so as to be accessible to the server which is indicative of at least the lowest bandwidth link between the server and the user equipment, and
   means for transmitting the dynamically generated content over the network to the web browser in the user equipment.

2. An information system as claimed in claim 1, wherein said network is an intranet of an organization and said means for dynamically generating content that is personalized to the user further takes into account user need information provided or stored so as to be accessible to the server which is indicative of at least the job of the user in the organization.

3. An information system as claimed in claim 1, wherein said network is an intranet of an organization and said means for dynamically generating content that is personalized to the user further takes into account user information provided or stored so as to be accessible to the server which is indicative of at least access rights of the user to confidential information maintained by the organization.

4. An information system as claimed in claim 1, wherein said means for dynamically generating content that is personalized to the user further takes into account user environment information provided or stored so as to be accessible to the server which is indicative of characteristics of the room in which the user equipment is located.

5. The system of claim 1 further comprising at least one database comprising computerized patient records, and wherein the dynamically generated content is provided from the at least one database.

6. The system of claim 1, wherein said means for dynamically generating content that is personalized to the user further takes into account the capabilities of the web browser.

7. The system of claim 1 wherein the means for dynamically generating content further comprises means for dynamically generating prioritized retrieval rules according to which the content is dynamically generated.

8. An information system comprising
   a network which is an intranet of an organization and
   at least one web server which is accessible via the network by a user at user equipment operating a web browser, which server comprises
   means for dynamically generating content, wherein the dynamically generated content comprises data retrieved from computer patient record information, wherein the dynamically generated content is personalized to the user taking into account user need information provided or stored so as to be accessible to the server which is indicative of at least the job of the user in the organization, and wherein the dynamically generated content comprises elements presentable to the user by the web browser operating in the user equipment, and
   means for transmitting the dynamically generated content over the network to the web browser in the user equipment, and
   wherein the transmitted and dynamically generated content is presented to the user by the web browser.

9. An information system as claimed in claim 8, wherein said means for dynamically generating content that is personalized to the user further takes into account user information provided or stored so as to be accessible to the server which is indicative of at least access rights of the user to confidential information maintained by the organization.

10. The system of claim 8 further comprising at least one database comprising computerized patient records, and wherein the dynamically generated content is provided from the at least one database.

11. The system of claim 8, wherein said means for dynamically generating content that is personalized to the user further takes into account the capabilities of the web browser.

12. The system of claim 8 wherein the means for dynamically generating content further comprises means for dynamically generating prioritized retrieval rules according to which the content is dynamically generated.

13. A method of providing content from a web server to web browsers of users over a network in response to user requests comprising:
   maintaining stored personalizing information for users;
   associating the personalizing information applicable to each individual user issuing a request for content; and
   dynamically generating in the web server the content provided in response to the request taking into account the associated personalizing information, wherein the personalizing information includes the lowest bandwidth link between the web server and the user's web browser, and transmitting the dynamically generated content over the network to the web browser.

14. A method of providing content as claimed in claim 13, wherein said network is an intranet of an organization and said personalizing information taken into account further includes the job of the user in the organization.

15. A method of providing content as claimed in claim 13, wherein said network is an intranet of an organization and said personalizing information taken into account further includes access rights of the user to confidential information maintained by the organization.

16. A method of providing content as claimed in claim 13, wherein said personalizing information taken into account further includes information which is indicative of characteristics of the room in which the user equipment is located.

17. The method of claim 13 wherein the step of dynamically generating in the web server the content further comprises providing the content from at least one database comprising computerized patient records.

18. The method of claim 13, wherein the personalizing information taken into account further includes the capabilities of web browsers.

19. The method of claim 13, wherein the step of dynamically generating in the web server content further comprises dynamically generating prioritized retrieval rules in response to each individual user request and according to which the content is dynamically generated.

20. The method of claim 19 wherein the step of dynamically generating prioritized retrieval rules further comprises:

dynamically generating rules for user privileges and access control, dynamically generating rules for user interests if the user is authorized to information according to the rules for user privileges and access control, and dynamically generating rules for the user environment if the user is authorized to and interested in information according to the rules for user privileges and access control and to the rules for user interests.

21. An information system comprising a network and at least one web server which is accessible via the network by a user at user equipment operating a web browser, which server comprises means for dynamically generating content, wherein the dynamically generated content comprises data retrieved from computer patient record information, wherein the dynamically generated content is personalized to the user taking into account the capabilities of the web browser, and wherein the dynamically generated content comprises elements presentable to the user by the web browser operating in the user equipment, and means for transmitting the dynamically generated content over the network to the web browser in the user equipment, and wherein the transmitted and dynamically generated content is presented to the user by the web browser.

22. A method of providing content from a web server to web browsers of users over a network in response to user requests comprising:

maintaining stored personalizing information for users;

associating the personalizing information applicable to each individual user issuing a request for content; and dynamically and automatically generating in the web server the content provided in response to the request, wherein the content is dynamically generated taking into account the associated personalizing information, by dynamically generating prioritized retrieval rules in response to each individual user request and according to which the content is dynamically generated, and wherein the dynamically generated content comprises elements presentable to the user by the web browser operating in the user equipment, transmitting the dynamically generated content over the network, and presenting the dynamically generated content to the user by the web browser.

23. The method of claim 22 wherein the step of dynamically generating further comprises retrieving at least a part of the content from computer patient record information.

* * * * *